(12) United States Patent
Lu et al.

(10) Patent No.: US 12,570,737 B2
(45) Date of Patent: Mar. 10, 2026

(54) LIQUID PREPARATION CONTAINING ANTI-IL-17 ANTIBODY

(71) Applicant: LIVZON MABPHARM INC., Zhuhai (CN)

(72) Inventors: Yi Lu, Zhuhai (CN); Jingyu Leng, Shanghai (CN); Denghui He, Zhuhai (CN); Huiyu Huang, Zhuhai (CN)

(73) Assignee: LIVZON MABPHARM INC., Zhuhai (CN)

( * ) Notice: Subject to any disclaimer, the term of this patent is extended or adjusted under 35 U.S.C. 154(b) by 946 days.

(21) Appl. No.: 17/756,896

(22) PCT Filed: Dec. 7, 2020

(86) PCT No.: PCT/CN2020/134170
§ 371 (c)(1),
(2) Date: Jun. 3, 2022

(87) PCT Pub. No.: WO2021/110164
PCT Pub. Date: Jun. 10, 2021

(65) Prior Publication Data
US 2023/0042795 A1 Feb. 9, 2023

(30) Foreign Application Priority Data
Dec. 6, 2019 (CN) .......................... 201911239277.9

(51) Int. Cl.
*C07K 16/24* (2006.01)
*A61K 9/00* (2006.01)
*A61K 39/00* (2006.01)

(52) U.S. Cl.
CPC .......... *C07K 16/244* (2013.01); *A61K 9/0019* (2013.01); *A61K 2039/505* (2013.01); *C07K 2317/565* (2013.01)

(58) Field of Classification Search
None
See application file for complete search history.

(56) References Cited

U.S. PATENT DOCUMENTS

| | | | | | |
|---|---|---|---|---|---|
| 10,442,857 | B2 * | 10/2019 | Ulitin | .......................... | A61P 11/06 |
| 10,858,427 | B2 * | 12/2020 | Dong | .......................... | A61P 37/00 |
| 11,801,300 | B2 * | 10/2023 | Joerg | .......................... | A61P 17/06 |
| 11,857,625 | B2 * | 1/2024 | Durran | .......................... | A61K 39/39591 |
| 12,296,008 | B2 * | 5/2025 | Joerg | .......................... | A61P 19/08 |
| 2012/0321553 | A1 * | 12/2012 | Zeng | .......................... | A61K 39/3955 424/85.7 |
| 2013/0209480 | A1 * | 8/2013 | Mpofu | .......................... | A61K 45/06 424/142.1 |
| 2017/0081401 | A1 * | 3/2017 | Ulitin | .......................... | C07K 16/244 |
| 2017/0368174 | A1 * | 12/2017 | Joerg | .......................... | A61P 17/06 |
| 2020/0031919 | A1 * | 1/2020 | Dong | .......................... | A61P 37/00 |
| 2021/0106683 | A1 * | 4/2021 | Durran | .......................... | A61K 47/183 |

FOREIGN PATENT DOCUMENTS

| | | |
|---|---|---|
| CN | 103189074 A | 7/2013 |
| CN | 107115526 A | 9/2017 |
| CN | 109745559 A | 5/2019 |
| WO | WO 2016/103153 A1 | 6/2016 |
| WO | WO 2018/161340 A1 | 9/2018 |
| WO | WO 2019/101582 A1 | 5/2019 |

OTHER PUBLICATIONS

NCBI Accession No. Q16552, Apr. 9, 2025, downloaded May 27, 2025.*
NBCI Accession No. Q96PD4, Apr. 9, 2025, downloaded May 27, 2025.*
Strickley et al., Journal of Pharmaceutical Sciences 110 (2021) 2590-2608.*
Internal Search Report of PCT/CN2020/134170, Mar. 8, 2021, 14 pages with English translation.
Written Opinion of PCT/CN2020/134170, Mar. 8, 2021, 4 pages.

* cited by examiner

*Primary Examiner* — Marianne P Allen
(74) *Attorney, Agent, or Firm* — Lewis Roca Rothgerber Christie LLP

(57) ABSTRACT

Provided is a liquid preparation containing an anti-IL-17 antibody at a concentration of 20 mg/mL to 200 mg/mL, a citrate buffer at a concentration of 10 mM to 50 mM, a sucrose at a concentration of 20 mg/mL to 120 mg/mL or arginine at a concentration of 50 mM to 250 mM, and polysorbate 80 at a concentration of 0.1 mg/mL to 5 mg/mL. In addition, the liquid preparation has a pH of 6.0±0.5, wherein the anti-IL-17 antibody is an anti-IL-17A/F monoclonal antibody. The liquid preparation can be a stable subcutaneous injection preparation, and can be used to treat IL-17A and/or IL-17F related diseases, such as psoriasis, psoriatic arthritis, ankylosing spondylitis, rheumatoid arthritis, multiple sclerosis, systemic lupus erythematosus, osteoarthritis or inflammatory bowel disease.

16 Claims, 4 Drawing Sheets

Specification includes a Sequence Listing.

Figure 1
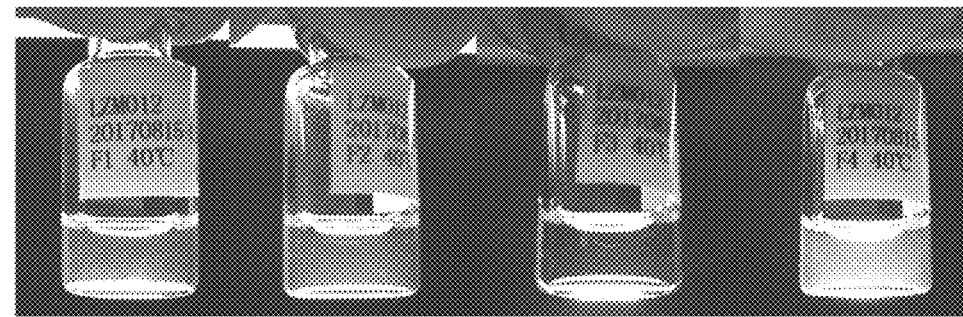
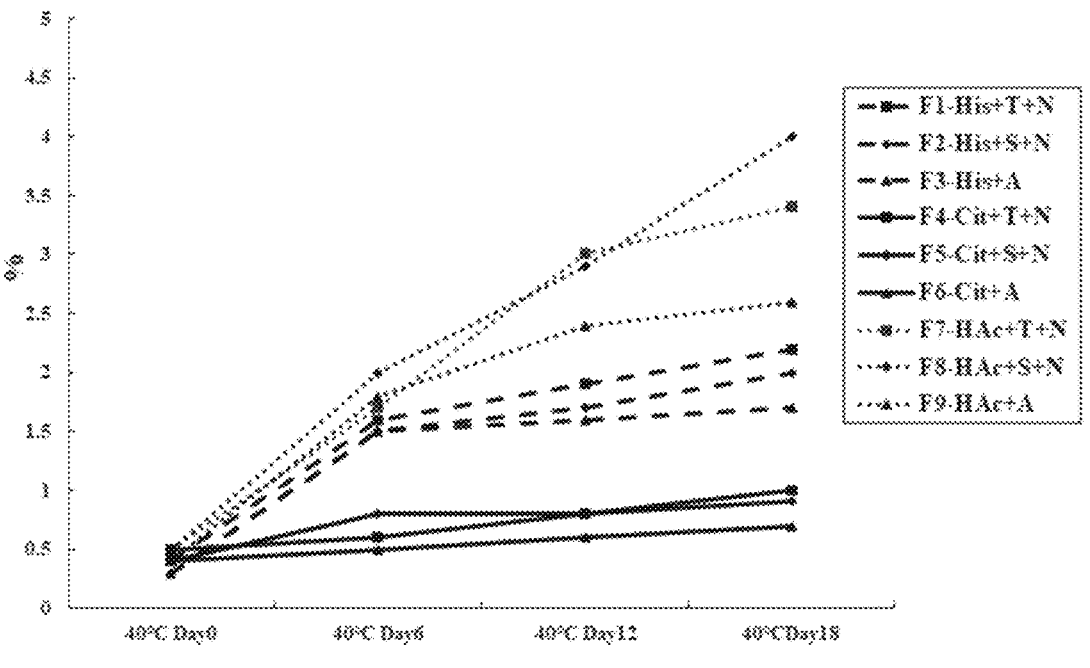
FIG. 2A

Figure 3
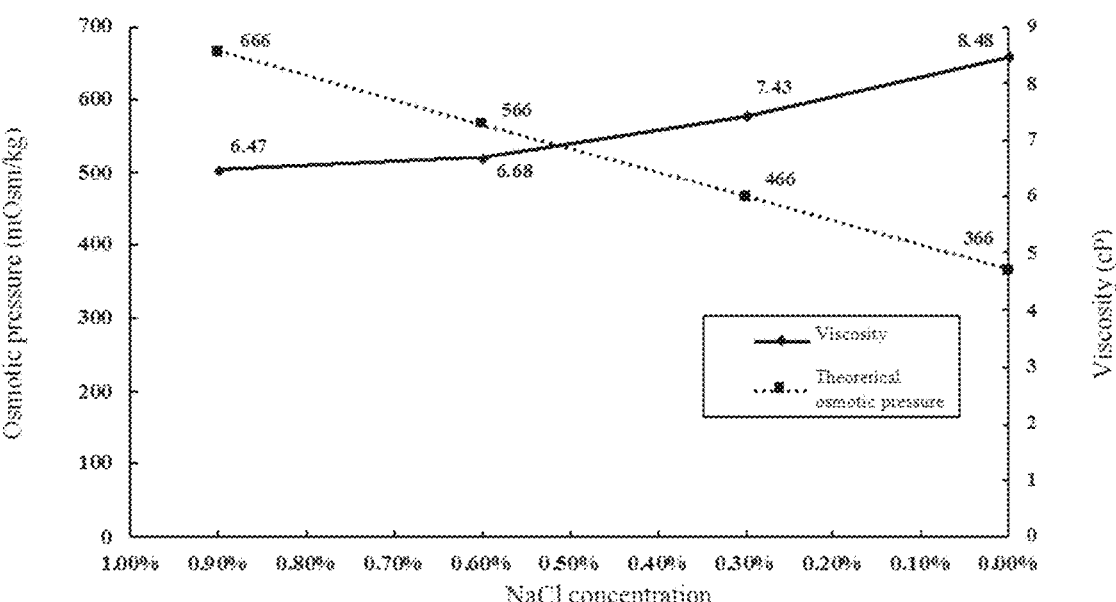
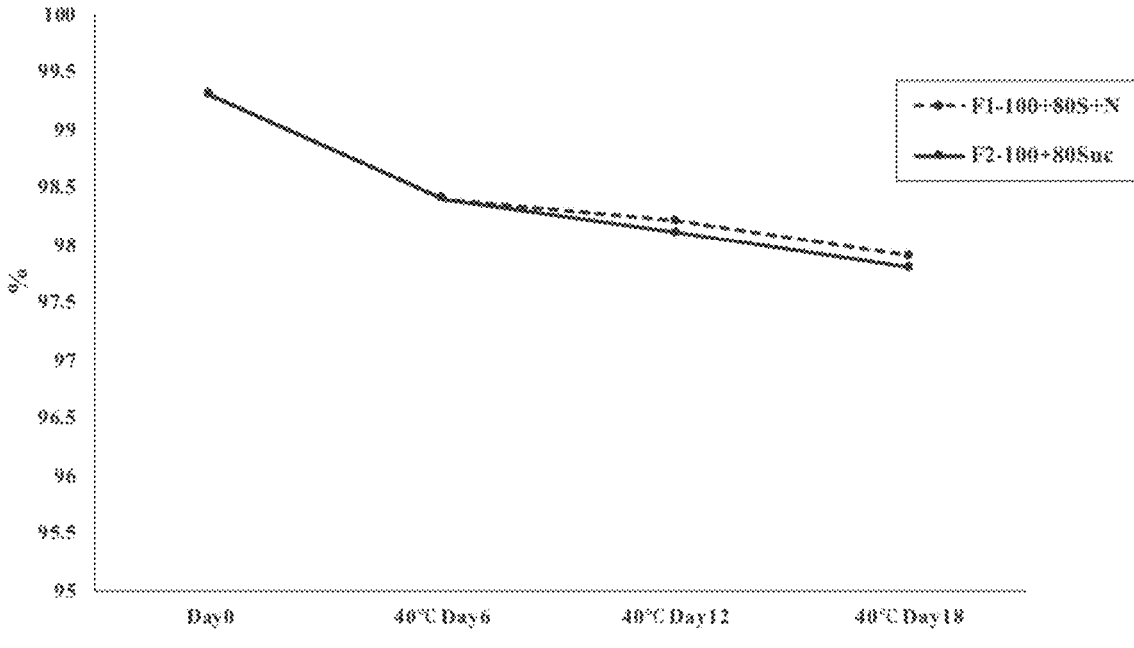
FIG. 4A

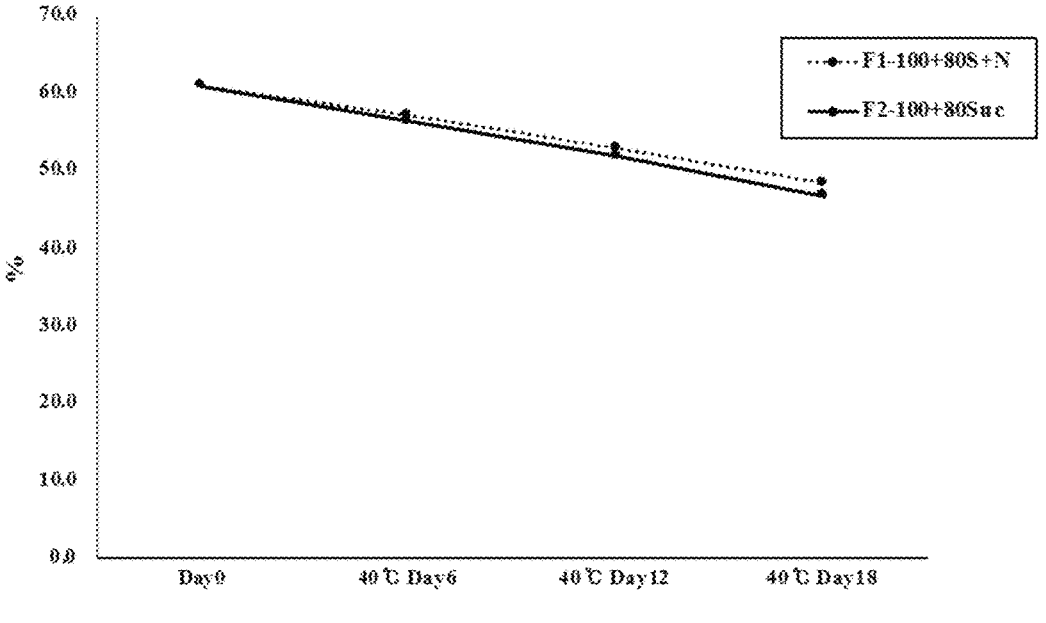
FIG. 4B
Figure 5
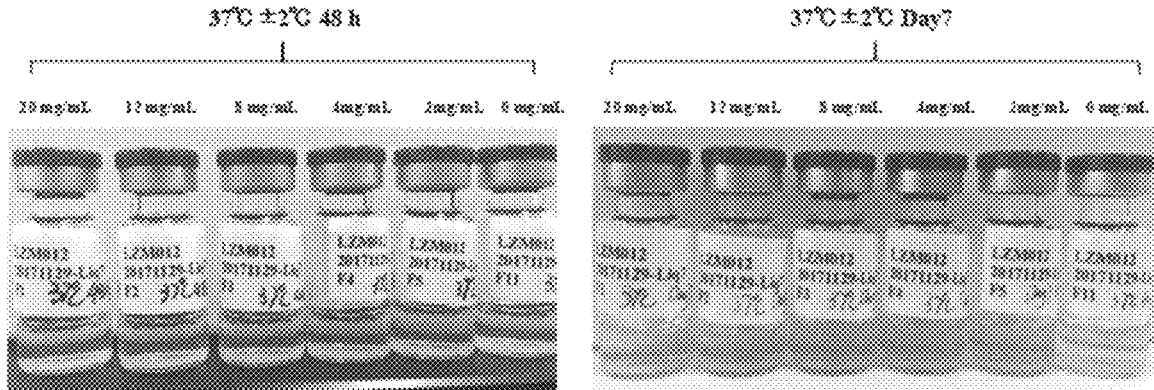

SEQUENCE LISTING

```
<160> NUMBER OF SEQ ID NOS: 10

<210> SEQ ID NO 1
<211> LENGTH: 10
<212> TYPE: PRT
<213> ORGANISM: artificial
<220> FEATURE:
<223> OTHER INFORMATION: CDR1H

<400> SEQUENCE: 1

Gly Tyr Thr Phe Thr Asp Tyr Asn Leu Asn
1               5                   10

<210> SEQ ID NO 2
<211> LENGTH: 17
<212> TYPE: PRT
<213> ORGANISM: artificial
<220> FEATURE:
<223> OTHER INFORMATION: CDR2H

<400> SEQUENCE: 2

Val Ile His Pro Asp Tyr Gly Thr Thr Ser Tyr Asn Gln Lys Phe Lys
1               5                   10                  15

Asp
```

<210> SEQ ID NO 3
<211> LENGTH: 9
<212> TYPE: PRT
<213> ORGANISM: artificial
<220> FEATURE:
<223> OTHER INFORMATION: CDR3H

<400> SEQUENCE: 3

Tyr Asp Tyr Gly Asp Ala Met Asp Tyr
1               5

<210> SEQ ID NO 4
<211> LENGTH: 16
<212> TYPE: PRT
<213> ORGANISM: artificial
<220> FEATURE:
<223> OTHER INFORMATION: CDR1L

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: artificial
<220> FEATURE:
<223> OTHER INFORMATION: CDR2L

<400> SEQUENCE: 5

Lys Val Ser Asn Arg Phe Ser
1               5

<210> SEQ ID NO 6
<211> LENGTH: 9
<212> TYPE: PRT
<213> ORGANISM: artificial
<220> FEATURE:
<223> OTHER INFORMATION: CDR3L

<400> SEQUENCE: 6

Ser Gln Ser Thr His Val Pro Leu Thr
1               5

<210> SEQ ID NO 7
<211> LENGTH: 118
<212> TYPE: PRT
<213> ORGANISM: artificial
<220> FEATURE:
<223> OTHER INFORMATION: VH

<400> SEQUENCE: 7

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asn Trp Val Arg Gln Ala Pro Gly Lys Gly Leu Glu Trp Met
        35                  40                  45

Gly Val Ile His Pro Asp Tyr Gly Thr Thr Ser Tyr Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

-continued

```
Val Arg Tyr Asp Tyr Gly Asp Ala Met Asp Tyr Trp Gly Gln Gly Thr
            100                 105                 110

Leu Val Thr Val Ser Ser
        115

<210> SEQ ID NO 8
<211> LENGTH: 112
<212> TYPE: PRT
<213> ORGANISM: artificial
<220> FEATURE:
<223> OTHER INFORMATION: VL

<400> SEQUENCE: 8

Asp Ile Val Met Thr Gln Ser Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Pro
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Leu Glu Ile Lys
            100                 105                 110

<210> SEQ ID NO 9
<211> LENGTH: 448
<212> TYPE: PRT
<213> ORGANISM: artificial
<220> FEATURE:
<223> OTHER INFORMATION: HC

<400> SEQUENCE: 9

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asn Trp Val Arg Gln Ala Pro Gly Lys Gly Leu Glu Trp Met
        35                  40                  45

Gly Val Ile His Pro Asp Tyr Gly Thr Thr Ser Tyr Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Tyr Asp Tyr Gly Asp Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175
```

-continued

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

<210> SEQ ID NO 10
<211> LENGTH: 219
<212> TYPE: PRT
<213> ORGANISM: artificial
<220> FEATURE:
<223> OTHER INFORMATION: LC

<400> SEQUENCE: 10

```
Asp Ile Val Met Thr Gln Ser Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Pro
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95
```

-continued

```
Thr His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

LIQUID PREPARATION CONTAINING ANTI-IL-17 ANTIBODY

CROSS-REFERENCE TO RELATED APPLICATIONS

The present application is a U.S. National Phase Patent Application of International Application Number PCT/CN2020/134170, filed on Dec. 7, 2020, which claims the priority benefit of Chinese Patent Application No. CN201911239277.9, filed on 6 Dec. 2019, the entire content of each of which is hereby incorporated by reference.

SEQUENCE LISTING

The instant application contains a Sequence Listing previously submitted to WIPO in ASCII format and the entire content of the electronic submission of the sequence listing is incorporated by reference in its entirety for all purposes. The ASCII file is named "LC20210012P-segl.txt," was last modified on Jun. 10, 2021, and is 9,400 bytes in size.

TECHNICAL FIELD

The present invention relates to the field of biopharmaceutical formulation, in particular to a stable liquid pharmaceutical formulation comprising an anti-IL-17 antibody.

BACKGROUND OF THE INVENTION

Anti-IL-17 monoclonal antibody drugs are known to be useful for the treatment of autoimmune diseases and inflammatory disorders and the like, such as psoriasis, psoriatic arthritis, ankylosing spondylitis, rheumatoid arthritis, multiple sclerosis, systemic lupus erythematosus, osteoarthritis or inflammatory bowel disease and the like, and patients can be effectively treated with subcutaneous injection of anti-IL-17 monoclonal antibody drugs.

Anti-H-17 monoclonal antibody drugs currently available on the market include Cosentyx, an anti-inflammatory drug from Novartis, and Taltz, an anti-inflammatory drug from Eli Lilly, each of which contains a monoclonal antibody against IL-17A (a subtype of IL-17) and is comprised of histidine or citrate buffer system, nonionic surfactant polysorbate 80 and a sugar alcohol stabilizer. It can be known from analysis of the formulations of the two drugs that:

(1) Cosentyx: currently there are two types of products, an injection pen or pre-filled needle and a lyophilized formulation. The formulation for injection pen or pre-filled needle comprises methionine, which acts primarily as an antioxidant. It is speculated the antibody molecule contains oxidation sites, which is a risk point of causing instability. A lyophilized formulation suffers from high manufacturing cost, complicated manufacturing process, cumbersome steps in use, and the like, and its use is not as convenient as a liquid formulation.

(2) Taltz: a high concentration (11.69 mg/mL) of NaCl is contained in the formulation, which is higher than isotonic saline (9 mg/mL NaCl). In addition, the citrate buffer system in the formulation is 0.51 mg/mL anhydrous citric acid and 5.11 mg/mL sodium citrate dihydrate (equivalent to 20 mM citrate buffer). The osmotic pressure of the drug formulation should be close to or greater than 400 mOsmol/kg according to theoretical calculation. A hypertonic solution when injected will cause temporary atrophy of red blood cells, and dehydration of blood cells and tissue cells, and thus an injection is generally required clinically to be an isotonic solution as much as possible. Therefore, the high osmotic pressure of Taltz poses a relatively great risk and disadvantages in its use. Furthermore, two doses of Taltz are required for once administration, so Taltz is inconvenient for application and of poor patient compliance.

Thus, there remains a need in the art for novel liquid formulations of anti-IL-17 antibodies, particularly anti-IL-17A/F antibodies.

SUMMARY OF THE INVENTION

The object of the present invention to provide a liquid formulation comprising an anti-IL-17 antibody, which allows the antibody to be stably present at a relatively high concentration and has viscosity as low as possible and an osmotic pressure which is close to isotonic.

The present invention provides the following technical solutions.

In one aspect, the present invention provides a liquid formulation comprising an anti-IL-17 antibody at a concentration ranging from 20 mg/mL to 200 mg/mL, citrate buffer at a concentration ranging from 10 mM to 50 mM, sucrose at a concentration ranging from 20 mg/mL to 120 mg/mL or arginine at a concentration ranging from 50 mM to 250 mM, and polysorbate 80 at a concentration ranging from 0.1 mg/mL to 5 mg/mL, and the liquid formulation has a pH value of 6.0±0.5.

IL-17 family includes members IL-17A, IL-17F, as well as IL-17B, IL-17C, IL-17D and IL-17E. In the liquid formulation provided by the present invention, the anti-IL-17 antibody is an anti-IL-17A/F antibody. With respect to sequence composition, the anti-IL-17 antibody according to the present invention comprises a heavy chain variable region (VH) and comprises in the heavy chain variable region CDR1 (CDR1H) as shown in SEQ ID NO: 1, CDR2 (CDR2H) as shown in SEQ ID NO: 2, and CDR3 (CDR3H) as shown in SEQ ID NO: 3; and comprises a light chain variable region (VL) and comprises in the light chain variable region CDR1 (CDR1L) as shown in SEQ ID NO: 4, CDR2 (CDR2L) as shown in SEQ ID NO: 5, and CDR3 (CDR3L) as shown in SEQ ID NO: 6.

Preferably, the anti-IL-17 antibody comprises a heavy chain variable region comprising an amino acid sequence as shown in SEQ ID NO: 7 and a light chain variable region comprising an amino acid sequence as shown in SEQ ID NO: S.

According to a particular embodiment of the present invention, the anti-IL-17 antibody comprises a heavy chain (HC) comprising an amino acid sequence as shown in SEQ ID NO: 9 and a light chain (LC) comprising an amino acid sequence as shown in SEQ ID NO: 10.

According to a particular embodiment of the present invention, the anti-IL-17 antibody is an anti-IL-17A/F monoclonal antibody comprising two heavy chains (HCs) each comprising an amino acid sequence as shown in SEQ ID NO: 9 and two light chains (LCs) each comprising an amino acid sequence as shown in SEQ ID NO: 10.

```
(CDR1H):
                                    SEQ ID NO: 1
GYTFTDYNLN (CDR2H):
                                    SEQ ID NO: 2
VIHPDYGTTSYNQKFKD
```

-continued (CDR3H):
SEQ ID NO: 3

YD YGDAMDY (CDR1L):
SEQ ID NO: 4

RSSQSLV HSNGNTYLH (CDR2L):
SEQ ID NO: 5

KVSNRFS (CDR3L):
SEQ ID NO: 6

SQSTHVP LT (VH):
SEQ ID NO: 7

QFQLVQSGAE VKKPGASVKV SCKASGYTFT DYNLNWVRQA

PGKGLEWMGV IHPDYGTTSY NQKFKDRVTM TVDTSTSTVY

MELSSLRSED TAVYYCVRYD YGDAMDYWGQ GTLVTVSS (VL):
SEQ ID NO. 8

DIVMTQSPLS LSVTPGQPAS ISCRSSQSLV HSNGNTYLHW

YLQKPGQPPQ LLIYKVSNRF SGVPDRFSGS GSGTDFTLKI

SRVEAEDVGV YYCSQSTHVP LTFGQGTKLE IK (HC):
SEQ ID NO: 9

QFQLVQSGAE VKKPGASVKV SCKASGYTFT DYNLNWVRQA

PGKGLEWMGV IHPDYGTTSY NQKFKDRVTM TVDTSTSTVY

MELSSLRSED TAVYYCVRYD YGDAMDYWGQ GTLVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKKVEPKS CDKTHTCPPC PAPELLGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKAIP APIEKTISKA KGQPREPQVY TLPPSRDELT

KNQVSLTCLV KGFYPSDIAV EWESNGQPEN NYKTTPPVLD

SDGSFFLYSK LTVDKSRWQQ GNVFSCSVMH EALHNHYTQK

SLSLSPGK (LC):
SEQ ID NO: 10

DIVMTQSPLS LSVTPGQPAS ISCRSSQSLV HSNGNTYLHW

YLQKPGQPPQ LLIYKVSNRF SGVPDRFSGS GSGTDFTLKI

SRVEAEDVGV YYCSQSTHVP LTFGQGTKLE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSFNRGEC

According to a particular embodiment of the present invention, the anti-IL-17 antibody according to the invention is a monoclonal antibody which comprises the sequences described above, and consists of two heavy chains and two light chains, the heavy chain of the antibody being as shown in SEQ ID NO: 9, and the light chain of the antibody being as shown in SEQ ID NO: 10. The sequences and preparation of the antibody are disclosed in PCT application publication WO2018161340A1.

Preferably, the concentration of the anti-IL-17 antibody ranges from 80 mg/mL to 130 mg/mL, preferably from 90 mg/mL to 110 mg/mL, and more preferably is 100 mg/mL.

Preferably, the concentration of the citrate buffer ranges from 15 mM to 30 mM, preferably from 15 mM to 25 mM, and more preferably is 20 mM. The citrate buffer is prepared from citric acid and sodium citrate di hydrate, and preferably consists of 0.66 mg/mL citric acid and 4.95 mg/mL sodium citrate dihydrate.

Preferably, the concentration of sucrose ranges from 60 mg/mL to 100 mg/mL, preferably from 70 mg/mL to 90 mg/mL, and more preferably is 80 mg/mL; alternatively, the concentration of arginine ranges from 80 mM to 200 mkt, preferably from 100 mM to 170 mM, and more preferably is 150 mM.

Preferably, the concentration of polysorbate 80 ranges from 0.1 mg/mL to 2.0 mg/mL, and more preferably is 0.5 mg/mL.

Preferably, the liquid formulation has a pH value of 6.0±0.3, preferably a pH value of 6.0.

Preferably, the liquid formulation provided by the present invention comprises no antioxidant, such as methionine; and comprises no viscosity reducer when the liquid formulation comprises sucrose, and in particular, the liquid formulation provided by the present invention does not comprise sodium chloride.

According to a particular embodiment of the present invention, the liquid formulation provided herein comprises the anti-IL-17 antibody at a concentration of 100 mg/mL, the citrate buffer at a concentration of 20 mM, sucrose at a concentration of 80 mg/mL, and polysorbate 80 at a concentration of 0.5 mg/mL; and the liquid formulation has a pH value of 6.0. Alternatively, the liquid formulation provided herein comprises the anti-IL-17 antibody at a concentration of 100 mg/mL, the citrate buffer at a concentration of 20 mM, arginine at a concentration of 150 mM, and polysorbate 80 at a concentration of 0.5 nag/mL; and the liquid formulation has a pH value of 6.0.

Also, according to a particular embodiment of the present invention, the liquid formulation provided herein consists of the ingredients described above with pH adjusted.

The liquid formulation provided by the present invention may be a pharmaceutical formulation of the anti-IL-17 antibody; and the liquid formulation may be in the form of a solution, an emulsion or a suspension, preferably is a solution.

Preferably, the liquid formulation or liquid pharmaceutical formulation may be a dosage form for parenteral administration, which may for example include dosage forms for intravenous, intramuscular, subcutaneous and intraperitoneal administration. Preferably, the liquid formulation of the present invention is an injection, in particular a subcutaneous injection.

In the context of the present invention, "antibody formulation" is used interchangeably with "liquid formulation of antibody".

In another aspect, the present invention provides use of the liquid formulation in the manufacture of a medicament for the treatment of a disease associated with IL-17A and/or IL-17F.

Preferably, the disease is selected from the group consisting of psoriasis, psoriatic arthritis, ankylosing spondylitis, rheumatoid arthritis, multiple sclerosis, systemic lupus erythematosus, osteoarthritis and inflammatory bowel disease.

In a further aspect, the present invention provides a method of treating a disease associated with IL-17A and/or IL-17F, the method including administering to a subject in need thereof an effective amount of the liquid formulation provided by the present invention.

Preferably, the disease is selected from the group consisting of psoriasis, psoriatic arthritis, ankylosing spondylitis, rheumatoid arthritis, multiple sclerosis, systemic lupus erythematosus, osteoarthritis and inflammatory bowel disease.

Preferably, the subject is a mammal, such as a primate, more preferably a human.

In yet another aspect, the present invention provides a container or a kit comprising the same, the container comprising the liquid formulation provided by the present invention.

The inventors of the present invention have successfully developed a new liquid antibody formulation directed to human IL-17A and/or IL-17F. The liquid formulation provided by the present invention comprises a relatively high concentration of an anti-IL-17A and/or IL-17F antibody, in particular an anti-H-17A/F monoclonal antibody, and when injected subcutaneously, the liquid formulation can provide high-dose antibody, and single dose per administration of the liquid formulation can satisfy the need for administration, thereby improving drug efficacy.

In particular, the liquid formulation provided by the present invention contains no antioxidant or viscosity reducer, yet allows the antibody to be stable at a relatively high concentration. In addition, the formulation itself has a low viscosity of less than 10 cP and a osmotic pressure close to isotonic, therefore the problems caused by injecting hypertonic solutions can be avoided, and a high patient compliance can be achieved.

BRIEF DESCRIPTION OF THE DRAWINGS

Embodiments of the present invention are described in detail below with reference to the attached figures, in which:

FIG. 1 shows the detection results of appearance and visible impurity inspection in pH screening of the antibody formulations in Example 1.

FIG. 3 shows theoretical osmotic pressure and viscosity of antibody formulations at different NaCl concentrations in Example 4, FIG. 4 shows the detection results of stability of formulations with and without NaCl in Example 4, in which panel 4A: SEC-HPLC, % Monomer, panel 4B: WCX-HPLC, % Main peak.

FIG. 5 shows the detection results of serum compatibility of antibody formulations in Example 5.

DETAILED DESCRIPTION OF PREFERRED EMBODIMENTS

Figure 2B:
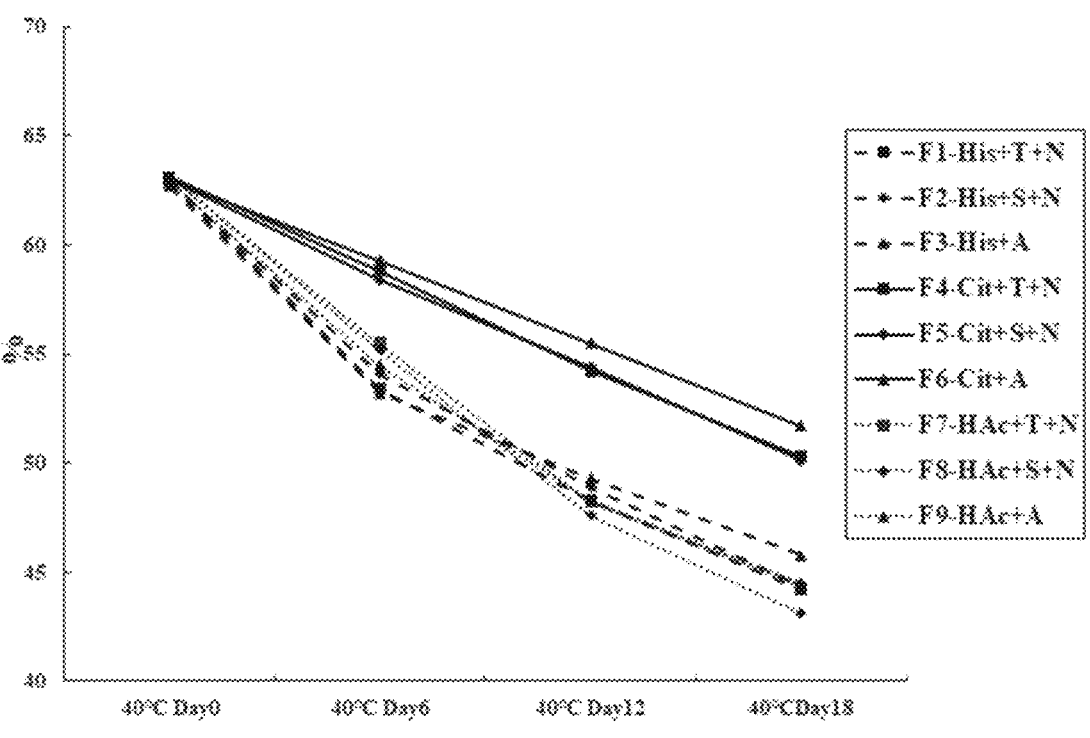
FIG. 2 shows the detection results of ingredient screening of antibody formulations in Example 3, in which panel 2A: SEC-HPLC, % Aggregate, panel 2B: WCX-HPLC, % Main peak, panel 2C: CE-SDS (non-reducing), % Purity.
Figure 2C:
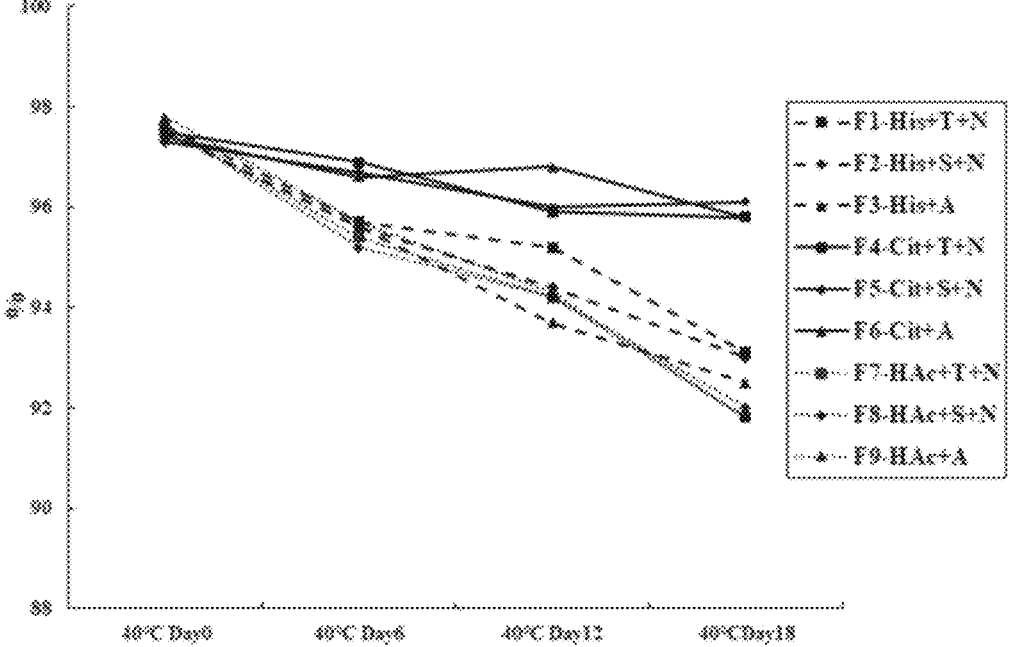

The present invention is illustrated below with reference to specific examples. It will be understood by those skilled in the art that these examples are merely illustrative of the present invention and do not limit the scope of the present invention in any way.

Experimental procedures in the following examples are all conventional ones, unless otherwise specified. Raw materials and reagents used in the following examples are all commercially available products, or can be prepared according to commonly known techniques in the art, unless otherwise specified.

A particular anti-IL-17N T monoclonal antibody is used in the following examples, the heavy chain of the antibody being as shown in SEQ ID NO: 9, and the light chain of the antibody being as shown in SEQ ID NO: 10. The sequences and preparation of the antibody are disclosed in PCT application publication WO2018161340A1, and the antibody is referred to herein simply as "LZM012".

Liquid formulations comprising the antibody are prepared according to the process as follows: if the formulation to be tested contains the same ingredients as LZM012 stock solution, an appropriate amount of the LZM012 stock solution is taken and then pH of the solution is adjusted using a pH adjuster, for example hydrochloric acid or sodium hydroxide, and antibody concentration of the solution is directly diluted to 100 mg/nil, with a formulation buffer; and if the formulation to be tested contains different ingredients from LZM012 stock solution, a purified intermediate (obtained after UF/DF and before adding a surfactant) is taken, and then excipients in the purified intermediate are replaced using ultrafiltration centrifugation, subsequently polysorbate 80 stock solution is added, and antibody concentration is adjusted to 100 mg/mL with a corresponding formulation buffer finally. The prepared liquid formulation is sterile filtered using a 0.22 μm filter, and filled into a container according to the filling volume as required correspondingly, which is in turn plugged and capped.

General methods involved in the examples include following ones.

DSC: The sample cell is soaked with a 10% solution of Decon 90 at 80° C. for 30 minutes, then is rinsed 2 times with Milli-Q water; and the injector is rinsed 2 times. Sample to be tested is diluted with LZM012 buffer (ingredients: 20 mM citrate buffer, 80 mg/mL sucrose, 0.5 mg/mL polysorbate 80, with pH corresponding to pH value in the screening condition) to an antibody concentration of 0.5 mg/mL and then centrifuged at 10,000 rpm for 2 minutes. Multiple buffer scans are performed to balance the instrument before the sample is scanned. Scan temperature ranges from 35-95° C. and scan rate is 90° C./h.

SEC-HPLC: performed according to General Rule 0512, Volume III, Pharmacopoeia of the People's Republic of China (2015 edition). TOSOH G3000SWxl column (5 μm, 7.8*300 mm) is used, with 0.1 mon $Na_2HPO_4$ (pH 6.5) and 0.2 mol/L NaCl as mobile phase; and the detection wavelength is set at 280 nm. Sample to be tested is diluted to an antibody concentration of about 1 mg/mL, to obtain a solution to be tested. 20 μL of the solution is injected into the liquid chromatograph, and relative content of monomer (reported value), relative content of aggregate (reported value), and relative content of fragment (reported value) are calculated by area normalization method.

WCX-HPLC: performed according to General Rule 0513, Volume III, Pharmacopoeia of the People's Republic of China (2015 edition). ProPac WCX-10 column is used, with a solution containing 20 mM MES and 20 mM NaCl as mobile phase A and a solution containing 20 mM. MES and 200 mM NaCl as mobile phase B. The flow rate is 1 mL/min, the column temperature is 25° C., and the detection wavelength is set at 280 nm; and gradient elution is conducted. Percentage of each of main peak, acidic peak and basic peak is calculated as percentage of peak area.

CE-SDS (non-reducing): in this procedure, an antibody is allowed to complex with the surfactant Sodium Dodecyl Sulfate (SDS); the sulfydryl in the antibody contained in sample to be tested and in a standard is alkylated using N-ethylmaleimide, and using linear high molecular mass gel solution as a sieving medium, fragments, intact proteins and aggregates can be separated based on their molecular weights in CE-SDS under high electric field. Retention time and relative intensity of fragments, intact proteins and aggregates are detected by a PDA detector using non-coated capillary (internal diameter: 50 μm; tube length: 30.2-31.0 cm; effective length: 20-21 cm; and detection window: 100 μm×200 μm) and a buffer (citrate-phosphate buffer, 1% SDS, pH 6.0). The sample is injected at 5 kv for 40 s and detected at a wavelength of 220 nm.

Visible impurity inspection: performed according to General Rule 0904, "Visible impurity inspection", Pharmacopoeia of the People's Republic of China (2015 edition).

IL-17A binding activity: Recombinant human IL-17A protein is solubilized at 0.5 μg/mL in PBS (10 mM, pH 7.4), and the obtained solution is added at 100 μL/well to a 96-well plate (Costar, Cat #: 9018), which is then sealed with sealing film and left at 5±3° C. overnight; subsequently, the plate is washed twice with PBST, blocking solution (PBST, containing 1% skim milk powder) is added at 300 μL/well into the plate, and the plate is shaking incubated at room temperature for 1.5 h. The sample to be tested, a standard, and a quality control are diluted to 500 ng/mL using PBST respectively, and subjected to 1.9 fold gradient dilution to obtain dilutions of concentrations ranging from 0.43 ng/mL-500 ng/mL. The dilutions of standard and sample to be tested are added at 100 μL/well to the blocked plate, which is then shaking incubated at room temperature for 2 h. Afterwards, the plate is washed 4 times with washing solution, and then horseradish peroxidase-labeled goat anti-human IgG (PBST, 1:80000) is added to the plate at 100 μL/well, which is then shaking incubated at room temperature for 1 h. Then the plate is washed with washing solution again, substrate solution is added at 100 μL/well, and the plate is placed in dark for 30 min before 50 μL stopping solution is added to stop the reaction. The absorbance is measured at 450 nm using a Microplate Reader with a reference wavelength of 620 nm. Measurement results are recorded, and specific activity s calculated (formula: 100%× EC50 of the standard/EC50 of the sample).

FlowCAM: Before loading any sample, the flow cell is first flushed with Milli-Q water for 3-9 passes until no particle is detected. Sample to be tested is 4-fold diluted with Milli-Q water, and allowed to rest at room temperature for 15 min. 500 mL of the dilution is used for the detection, and particles in the range of 2 μm to 2000 μm are detected.

LC-MS (oxidation detection): an appropriate amount of a sample is taken, subjected to processing including denaturing, reducing, alkylating, and desalting, and then trypsin is added for digestion; and the obtained sample is injected into a UPLC sample vial, and analyzed by UPLC-MS. Experimental data is processed using Waters' MassLynx 4.1 software and oxidation ratio is calculated by extracting ion mobility spectrometry (EIC).

Viscosity detection: Samples are detected using a Brookfield DV-III rheometer. After zeroing using a standard, 0.5-1.0 mL of a sample is added and an appropriate speed is selected to ensure a torque in the range of 10% to 100% and viscosity value is read.

Example 1 PH Screening (LIM012 20170815-Liq1)

PH screening experiment for Ln/1012 formulation was based on a platform formulation (100 mg/mL LZM012, 25 mM histidine. 80 mg/mL trehalose, 0.5 mg/mL polysorbate

8

80) and a series of pH levels (5.0, 5.5, 6.0, 6.5) were designed, in order to screen out the most suitable pH value.

Formulation Design is Shown in Table 1.

TABLE 1

| LZM012 formulations | | |
|---|---|---|
| | LZM012 | pH |
| F1 | 100 mg/mL | 5.0 |
| F2 | | 5.5 |
| F3 | | 6.0 |
| F4 | | 6.5 |

On an ultra-clean bench, 12 mL of the platform formulation at pH 5.5 was taken and 0-300 μL of either 0.5 M HCl or 0.5 M NaOH solution was added into the formulation to adjust the pH to 5.0, 5.5, 6.0, or 6.5 respectively. The formulations were sterile filtered using a 0.22 μm filter, and each was filled into a 2-mL vial for injection at a filing volume of 1 mL, which was then plugged and capped.

DSC detection results are provided in Table 2, which showed: over the pH range of 5.0-6.5, Tonset and Tint increased with pH value increased; there was essentially no significant difference in Tm2 between groups of pH 5.5 to pH 6.5, and there was a slight decrease in Tm2 (Fab) (1-2° C.) of the formulation at pH 5.0. Therefore, LZM012 molecule has an optimal thermal stability in the pH range of 5.5-6.5,

TABLE 2

| DSC detection results of LZM012 formulations | | | |
|---|---|---|---|
| F | Tonset (° C.) | Tm1 (° C.) | Tm2 (° C.) |
| F1-pH 5.0 | 57.56 | 65.92 | 81.25 |
| F2-pH 5.5 | 61.14 | 69.50 | 83.44 |
| F3-pH 6.0 | 63.63 | 71.99 | 83.14 |
| F4-pH 6.5 | 64.18 | 73.92 | 83.68 |

In addition, stability experiments shown in Table 3 were performed under accelerated condition at 40° C. (40° C.±2° C.).

SEC-HPLC detection results showed that more aggregates were detected at pH 6.5 and pH 5.0, and preferred pH range with less aggregates was pH 5.5 to pH 6.0.

WCX-HPLC and nR CE-SDS detection results showed no significant difference in surface charge and purity over pH 5.0-6.5.

Detection results of appearance and visible impurity inspection are shown in FIG. 1. The results showed that under accelerated condition of 40° C. for 11 days, protein aggregation particles appeared in varying degrees in the formulations at pH 5.0, pH 5.5 and pH 6.5. Among the formulations, more aggregates existed in the formulations at pH 5.0 and pH 6.5 in which smoky aggregation was visible; in contrast, the formulation at pH 6.0 was clear and transparent. Therefore, pH 6.0 is more favorable to maintain the native conformation of the protein.

The detection results of binding activity to IL-17 showed no significant difference in activities of the formulations at pH 5.0, pH 5.5 and pH 6.5 at zero hour after preparation and at Day 11 under accelerated condition of 40° C.

Sub-visible particle (FlowCAM) detection results showed no significant difference in the sub-visible particles in the formulations at pH 5.0, pH 5.5 and pH 6.5 at zero hour after preparation, and at Day 11 and Day 20 under accelerated condition of 40° C.

Data in detail is provided in Table 3.

TABLE 3

| | | Day 0 | | | | 40° C. Day 11 | | | | 40° C. Day20 | | | |
|---|---|---|---|---|---|---|---|---|---|---|---|---|---|
| | | F1 pH 5.0 | F2 pH 5.5 | F3 pH 6.0 | F4 pH 6.5 | F1 pH 5.0 | F2 pH 5.5 | F3 pH 6.0 | F4 pH 6.5 | F1 pH 5.0 | F2 pH 5.5 | F3 pH 6.0 | F4 pH 6.5 |
| SEC-HPLC | Monomer | 98.8 | 99.7 | 99.5 | 99.1 | 94.9 | 96.0 | 95.2 | 94.3 | 91.2 | 92.0 | 90.8 | 88.8 |
| (%) | Aggregate | 1.2 | 0.3 | 0.5 | 0.9 | 3.1 | 2.2 | 2.2 | 2.5 | 5.4 | 4.6 | 4.9 | 5.2 |
| | Degradation | N.D. | N.D. | N.D. | N.D. | 2.0 | 1.8 | 2.7 | 3.2 | 3.4 | 3.4 | 4.3 | 6.0 |
| nR CE- | Purity | 97.1 | 97.0 | 97.2 | 97.0 | 94.4 | 95.2 | 94.1 | 92.1 | 91.1 | 90.7 | 89.3 | 88.1 |
| SDS | Fragment | 2.9 | 2.9 | 2.8 | 3.0 | 5.1 | 4.4 | 5.5 | 7.5 | 7.1 | 7.5 | 8.9 | 10.2 |
| (%) | Aggregate | N.D. | N.D. | N.D. | N.D. | 0.6 | 0.4 | 0.4 | 0.4 | 1.8 | 1.8 | 1.9 | 1.7 |
| WCX- | Main peak | 62.6 | 63.3 | 62.6 | 62.51 | 48.7 | 48.5 | 49.3 | 49.7 | 41.3 | 40.7 | 41.5 | 40.5 |
| HPLC, before | Acidic peak | 16.7 | 16.9 | 17.2 | 17.6 | 30.2 | 32.8 | 32.7 | 33.1 | 38.2 | 41.3 | 41.9 | 43.9 |
| enzymatic digestion (%) | Basic peak | 20.7 | 19.8 | 20.2 | 19.9 | 21.1 | 18.6 | 18.0 | 17.3 | 20.5 | 17.9 | 16.6 | 15.6 |
| Binding activity to IL-17 (%) | | 102 | 105 | 103 | 93 | 103 | 101 | 103 | 102 | / | / | / | / |
| FlowCAM | 2-10 μm | 3161 | 6141.5 | 7026 | 9875.5 | 28511 | 7622 | 17389 | 8980 | 1542 | 5155 | 9280 | 9092 |
| (%) | 10-25 μm | 151 | 433 | 254.5 | 564 | 1733 | 568 | 970.5 | 719 | 363 | 446 | 522 | 658 |
| | >25 μm | 10 | 0 | 22 | 60.5 | 194.5 | 86.5 | 108 | 72 | 76 | 53 | 15 | 38 |

Thus, it can be seen from a comprehensive analysis on the above results that the thermal stability of the molecule is best in the range of pH 5.5-6.5, according to DSC results; while the best purity and appearance are achieved at pH 5.5-6.0. So comprehensively the pH should be centered in the range of pH 5.5-6.0, and a pH value as close to 6.0 as possible is better. Therefore, pH 6.0±0.3 can be determined.

Example 2 Viscosity Study (LZM012 20170829-Liq3)

Study found that LZM012 exhibited high protein hydrophobicity, and the platform formulation (100 mg/mL LMZ012, 25 mM histidine, 80 mg/mL trehalose, 0.5 mg/mL polysorbate 80, pH 6.0) contained a relatively high concentration of LMZ012, and was detected to have a viscosity of 14 cP, exceeding the internal control standard which was 10 cP. Therefore, a viscosity reducer was considered to be added into the formulation, to reduce the viscosity of the formulation.

The present example provides researches on the ability of two excipients, NaCl and arginine, to reduce viscosity. Formulations and viscosity detection results thereof are provided in Table 4.

TABLE 4

Viscosity detection results in LZM012 20170829-Liq3

| F | Formulation | Viscosity (cP) |
|---|---|---|
| F1-NaCl | 100 mg/mL LZM012, 25 mM histidine, 80 mg/mL trehalose, 9 mg/mL NaCl, 0.5 mg/mL polysorbate 80 | 5.8 |
| F2-Arginine | 100 mg/mL LZM012, 25 mM histidine, 80 mg/mL trehalose, 100 mM arginine, 0.5 mg/mL polysorbate 80 | 5.5 |
| F3-control | 100 mg/mL LZM012, 25 mM histidine, 80 mg/mL trehalose, 0.5 mg/mL polysorbate 80 | 13.9 |

Formulations F1, F2, and F3 shown in Table 4 were prepared by adding appropriate amounts of the LZM012 stock solution (130 mg/mL LZM012, 25 mM histidine, 80 trehalose, 0.5 mg/mL polysorbate 80) into formulation buffer 1 (25 mM histidine, 80 mg/mL trehalose, 39.15 mg/mL NaCl, 0.5 mg/mL, polysorbate 80), formulation buffer 2 (25 mM histidine, 80 mg/mL trehalose, 432 mM arginine, 0.5 mg/mL, polysorbate 80), and formulation buffer 3 (25 mM histidine, 80 mg/mL trehalose, 0.5 mg/mL polysorbate 80), respectively.

The detections results showed that both 9 mg/mL NaCl and 100 mM arginine were able to reduce the viscosity of the LZM012 formulations to below 10 cP, exhibiting no significant difference in their viscosity reducing ability. Thus, both NaCl and arginine were selected to be used as the viscosity reducer for a LZM012 formulation.

Example 3 Ingredient Screening (LZM012 20170925-Liq4)

It is known from biological products marketed both at home and abroad that polysorbate 80 (PS80) is frequently used at a concentration ranging from 0.05 mg/mL to 2 mg/mL, According to that concentration range, 0.5 mg/mL, PS80 was selected and added to a LZM012 formulation, to solubilize the protein and prevent the protein from aggregation and adsorption.

On the basis of the determination of pH 6.0, and 0.5 mg/mL PS80, types of buffer system and stabilizer were screened next. Mainly, 3 buffer systems, i.e., histidine, citrate and acetate (HAc), and 3 stabilizers, i.e., trehalose, sucrose and arginine were investigated. Since LZM012 had a high viscosity, 9 mg/mL NaCl was added to the formulations containing no arginine in the present example to reduce viscosity. Ingredients of the formulations in detail are provided in Table 5.

TABLE 5

Formulations in LZM012 20170925-Liq4

| F | LZM012 | pH Buffer | Stabilizing agent | Surfactant |
|---|---|---|---|---|
| F1 | 100 mg/mL | 6.0 25 mM histidine | 80 mg/mL trehalose, 0.9% NaCl | 0.5 mg/mL Polysorbate 80 |
| F2 | 100 mg/mL | 6.0 25 mM histidine | 80 mg/mL sucrose, 0.9% NaCl | 0.5 mg/mL Polysorbate 80 |
| F3 | 100 mg/mL | 6.0 25 mM histidine | 150 mM arginine | 0.5 mg/mL Polysorbate 80 |
| F4 | 100 mg/mL | 6.0 20 mM citrate | 80 mg/mL trehalose, 0.9% NaCl | 0.5 mg/mL Polysorbate 80 |
| F5 | 100 mg/mL | 6.0 20 mM citrate | 80 mg/mL sucrose, 0.9% NaCl | 0.5 mg/mL Polysorbate 80 |
| F6 | 100 mg/mL | 6.0 20 mM citrate | 150 mM arginine | 0.5 mg/mL Polysorbate 80 |
| F7 | 100 mg/mL | 6.0 20 mM HAc | 80 mg/mL trehalose, 0.9% NaCl | 0.5 mg/mL Polysorbate 80 |
| F8 | 100 mg/mL | 6.0 20 mM HAc | 80 mg/mL sucrose, 0.9% NaCl | 0.5 mg/mL Polysorbate 80 |
| F9 | 100 mg/mL | 6.0 20 mM HAc | 150 mM arginine | 0.5 mg/mL Polysorbate 80 |

An appropriate amount of the purified intermediate of LZM012 was taken and subjected to buffer replacement using ultrafiltration centrifugation according to Table 5. The protein concentration in the solution obtained after buffer replacement was adjusted to 100 mg/mL using corresponding formulation buffers respectively. Each of the formulations prepared was sterile-filtered through a 0.22 μm filter and filled into a vial for injection, which was then plugged and capped.

Stability experiments as follows were performed under accelerated condition at 40° C. (40° C.±2° C.).

SEC-HPLC detection results are shown in panel 2A, which showed that aggregate contents in the formulations containing histidine and acetate buffer systems were significantly higher than those formulations containing citrate buffer, which indicated that the citrate buffer system was more favorable for the molecule stability of LZM012; furthermore, no significant difference in aggregate content was observed between the formulations containing the 3 different stabilizers with citrate buffer system.

WCX-HPLC detection results are shown in panel 2B, which showed that percentages of main peak of the formulations containing histidine and acetate buffer systems were significantly lower than the formulations containing citrate; furthermore, no significant difference in percentage of main peak was observed between the formulations containing the 3 different stabilizers with citrate buffer system.

NR CE-SDS detection results are shown in panel 2C, which showed that purities of the formulations containing histidine and acetate buffer systems were significantly lower than the formulations containing citrate; furthermore, no significant difference in purity was observed between the formulations containing the 3 different stabilizers with citrate buffer system.

In summary, a citrate buffer system was selected as the buffer for a formulation of LZM012. The three stabilizers do not significantly differ in maintaining protein stability of LZM012, but when a citrate buffer was identified as the buffer system to be used, a saccharide could somewhat relieve the injection pain caused by the citrate buffer. Therefore, sucrose or trehalose is preferably used as the stabilizer for LZM012 formulation; but arginine can be used too. Sucrose costs less than trehalose in comparison, so starting by economic benefits, sucrose can be selected as a stabilizer for LZM012 formulation.

Example 4 Study on Viscosity Reducer in Citrate Buffer System 4.1 Effects of Different Concentrations of NaCl on the Viscosity of a LZM012 Formulation A preferred formulation was determined through the ingredient screening in Liq4 provided in Example 3: 100 mg/mL LZM012, 20 mM citrate buffer, 80 mg/mL sucrose, 9 mg/mL NaCl, 0.5 mg/MI, PS80, pH 6.0, and the osmotic pressure of the formulation was 666 mOsm/kg. The present example provides researches on the effects of different concentrations of sodium chloride (9, 6, 3, and 0 mg/mL NaCl) on the viscosity of a LZM012 formulation which was based on the preferred formulation.

The formulation of 100 mg/mL LZM012, 20 mM citrate buffer, 80 mg/mL sucrose, 0.5 mg/mL PS80, pH 6.0 was selected and solid NaCl was added into the formulation to adjust NaCl content in the formulation to 9, 6, 3, or 0 mg/mL.

Viscosity detection results of the formulations containing different concentrations of sodium chloride are shown in FIG. 3, which showed that the viscosity of the formulation increased with the NaCl concentration increased. When the sodium chloride was completely absent, the viscosity of the solution was 8.48 cP, and the theoretical osmotic pressure of the solution was close to isotonic. Comparing with the experiment results in Liq3 provided in Example 2 (the formulation contained 100 mg/mL LZM012, 25 mM histidine, 80 mg/mL trehalose, 0.5 mg/mL polysorbate 80, pH 6.0, having viscosity of 14 cP), the results indicated that citrate buffer itself has a viscosity reducing ability. Therefore; no viscosity reducer such as NaCl or the like needs to be added into a LZM012 formulation if citrate is used as a buffer system for LZM012, and the viscosity of the formulation can meet the internal control standard (≤10 cP).

4.2 Effect on Stability by the Absence of NaCl (LZM012 20171115-Liq5)

Based on the formulation screened out in the ingredient screening in Liq4, stabilities of a formulation containing 9 mg/mL NaCl and a formulation containing no NaCl were compared, to investigate whether the absence of NaCl would affect the stability of the LZM012 molecule.

Formulation F1: 100 mg/mL LZM012, 20 mM citrate buffer, 80 mg/mL sucrose, 9 mg/mL NaCl, 0.5 mg/mL PS80, pH 6.0;

Formulation F2: 100 mg/mL LZM012, 20 mM citrate buffer, 80 mg/mL sucrose, 0.5 mg/mL PS80, pH 6.0.

An appropriate amount of NaCl was added into a LZM012 formulation (100 mg/mL LZM012, 20 mM citrate buffer, 80 mg/nit, sucrose, 0.5 mg/mL PS80, pH 6.0) to adjust the NaCl concentration to 9 nag/mL and Formulation F1 was then obtained. Ingredients of formulation F2 are the same as those of the LZM012 formulation.

SEC-HPLC and WCX-HPLC detections results are shown in panel 4A and panel 4B, respectively, which showed that the presence or absence of sodium chloride had no Obvious effect on the stability of the LZM012 molecule.

4.3 A Brief Summary of the Viscosity Reducer NaCl

It can be determined from the investigations on viscosity and stability that no viscosity reducer such as NaCl or the like needs to be added into a LZM012 formulation containing 100 mg/mL antibody when citrate is used as a buffer system therein. Therefore, the LMZ012 formulation finally is determined as: 100 mg/mL LZM012, 20 mM citrate buffer, 80 mg/mL sucrose, 0.5 mg/mL PS80, pH 6.0; or, 100 mg/mL LZM012, 20 mM citrate buffer, 150 mM arginine, 0.5 mg/mL PS80, pH 6.0.

Example 5 Serum Compatibility Study (LZM012 20171129-Liq7)

After an injection containing a drug is subcutaneously injected into a human body, it will be instantaneously diluted by serum, thereafter gradually absorbed by the human body, and the concentration of the drug will decease gradually. In the study provided in the present example, human serum was used to dilute the 100 nag/mL LZM012 formulation to a series of protein concentrations (20 mg/mL, 12 mg/mL, 8 mg/mL, 4 mg/ML, 2 mg/mL, 0 mg/mL), to simulate the process by which the 100 mg/mL LZM012 formulation is gradually absorbed upon subcutaneous injection. Changes of samples at 37° C. 2° C. were monitored by visible impurity inspection to investigate the compatibility of the LZM012 protein with human serum.

The detection results of visible impurity inspection of the samples accelerated at 37° C. 2° C. for 48 hours and for 7 days are shown in FIG. 5, which showed that in the range of 2 mg/mL to 20 mg/mL LZM012, no significant difference in appearance between the LZM012 solutions prepared with human serum and the serum control was observed during the period of investigation, and all the LZM012 solutions were transparent without precipitation. Therefore, in the established formulation (100 mg/mL LZM012, 20 mM citrate buffer, 80 mg/mL sucrose, 0.5 mg/mL PS80, pH 6.0), the LZM012 molecule exhibits a good compatible with human serum.

In conclusion; a formulation of LZM012 is ultimately determined to be: 100 mg/mL recombinant humanized anti-human IL-17 AN monoclonal antibody LZM012, 20 mM citrate buffer (0.66 mg/mL citric acid ($C_6H_8O_7.H_2O$), 4.95 mg/mL sodium citrate ($C_6H_5O_7Na_3.2H_2O$)), 80 mg/mL sucrose ($C_{12}H_{22}O_{11}$), and 0.5 mg/mL polysorbate 80, pH 6.0±0.3.

Example 6 Oxygen Research (LZM012 20170829-Liq 2)

The LZM012 formulation is a subcutaneous injection which will be exposed to air for a prolonged period of time during production and storage. The present example provides researches on the effect of oxygen on the stability of the molecule in the LZM012 formulation, which results were used as a reference to decide whether an antioxidant should be added to the formulation.

A pilot production sample was prepared with the final formulation of LZM012 (100 mg/mL LZM012, 20 mM citrate buffer, 80 mg/mL sucrose, 0.5 mg/mL polysorbate 80, pH 6.0), and pure oxygen was fed into the production sample of LZM012 (F1), The process of feeding oxygen lasted 20 minutes to saturate the oxygen content of the formulation, and then the obtained sample was placed in an incubator at 25° C.±2° C. along with an untreated control (F2) for stability testing.

The stability testing results are provided in Table 6.

TABLE 6

Accelerated stability data of the LZM012 formulation (final formulation) under oxidative condition

| Test items | | Day 0 | Day 2 | 25° C. | | 25° C. 1W | |
|---|---|---|---|---|---|---|---|
| | | | | F1-$O_2$ | F2-control | F1-$O_2$ | F2-control |
| SEC (%) | Monomer | 99.2 | 99.2 | 99.2 | 99.2 | 99.2 | 99.2 |
| | Aggregate | 0.7 | 0.7 | 0.7 | 0.7 | 0.7 | 0.7 |
| | Degradation | <0.4 (LOD) | <0.4 (LOD) | <0.4 (LOD) | <0.4 (LOD) | <0.4 (LOD) | <0.4 (LOD) |
| nR CE-SDS (%) | Purity | 96.7 | 96.6 | 96.6 | 96.5 | 96.5 | |
| | Fragment | 3.3 | 3.4 | 3.4 | 3.5 | 3.5 | |
| | Aggregate | N.D. | N.D. | N.D. | N.D. | N.D. | |
| WCX-HPLC, before enzymatic digestion (%) | Main peak | 59.8 | 59.8 | 60 | 59.8 | 59.3 | |
| | Acidic peak | 19.5 | 19.5 | 19.7 | 20.1 | 19.8 | |
| | Basic peak | 20.8 | 20.7 | 20.4 | 20.1 | 20.9 | |
| FlowCAM (P/mL) | 2-10 μm | 1129 | 492 | 178 | 110 | 153 | |
| | 10-25 μm | 59 | 34 | 34 | 0 | 0 | |
| | >25 μm | 0 | 8 | 0 | 0 | 0 | |
| Oxidation* | M105 (2T11) | 5.0% | 5.0% | 5.0% | 5.0% | 5.0% | |
| | M253 (2T20) | 6.4% | 6.7% | 7.0% | 6.8% | 6.5% | |

*the numbers following M represent the positions of methionine in the peptide chains, the numbers preceding T represent the light or heavy chain (1 represents light chain, and 2 represents heavy chain), and T and the numbers following T represent which peptide fragment obtained by enzymatic digestion. For example: 1T1 means the first peptide fragment of the light chain.

Results showed no significant difference with respect to those physical and chemical analytical indicators between the oxygen treatment experimental group (F1-O$_2$) and the control group (F2-control); and the mass spectrometric analysis showed for the 2 Met species in LZM012 which are relatively relevant to oxidation, no significant difference in the oxidation between the two groups was observed (a change above 2% means a significant difference). Therefore, no antioxidant needs to be added to the formulation of LZM012.

Example 7 Activity Detection of LZM012 Formulation

Three pilot production samples were prepared with the final formulation by an optimized process, and their activities were detected and provided in Table 7. It can be seen that the formulation is still effective and has biological activity under long term and accelerated conditions.

TABLE 7

Data of binding activity of LZM012 in pilot production batches to IL-17A

| Batch No. | Zero hour | Long term stability (5° C. ± 3° C.) | | | Accelerated stability (25° C. ± 2° C.) | | | |
| | | 3 months | 6 months | 9 months | 1 month | 2 months | 3 months | 6 months |
| --- | --- | --- | --- | --- | --- | --- | --- | --- |
| 201801003 | 99% | 96% | 99% | 101% | 102% | 94% | 95% | 96% |
| 201804009 | 93% | 105% | 97% | 96% | 105% | 97% | 97% | 96% |
| 201804010 | 102% | 99% | 100% | 99% | 98% | 101% | 99% | 94% |

Note:
an acceptable standard for activity is: relative activity compared to an analytical standard should be 70% to 130%.

The above description of the embodiments of the present invention is not intended to limit the present invention, and those skilled in the art may make various changes and modifications to the present invention without departing from the spirit of the present invention, which should fall within the scope of the appended claims.

What is claimed is:

1. A liquid formulation comprising:
   an anti-IL-17 antibody at a concentration ranging from 90 mg/ml to 110 mg/mL, wherein the anti-IL-17 antibody is an anti-IL-17A/F monoclonal antibody comprising two heavy chains (HCs) each comprising an amino acid sequence as shown in SEQ ID NO: 9 and two light chains (LCs) each comprising an amino acid sequence as shown in SEQ ID NO: 10;
   citrate buffer at a concentration ranging from 15 mM to 25 mM;
   sucrose at a concentration ranging from 70 mg/mL to 90 mg/ml or arginine at a concentration ranging from 100 mM to 150 mM; and
   polysorbate 80 at a concentration ranging from 0.1 mg/ml to 0.5 mg/mL,
   wherein the liquid formulation has a pH value of 6.0±0.3, and
   wherein the liquid formulation does not comprise sodium chloride.

2. The liquid formulation according to claim 1, wherein the concentration of the anti-IL-17 antibody is 100 mg/mL.

3. The liquid formulation according to claim 1, wherein the concentration of the citrate buffer is 20 mM.

4. The liquid formulation of claim 3, wherein the concentration of sucrose is 80 mg/ml;
   alternatively, the concentration of arginine is 150 mM.

5. The liquid formulation according to claim 3, wherein the citrate buffer is a citric acid-sodium citrate buffer.

6. The liquid formulation according to claim 3, wherein the citrate buffer consists of 0.66 mg/mL citric acid and 4.95 mg/mL sodium citrate dihydrate.

7. The liquid formulation according to claim 1, wherein the concentration of polysorbate 80 is 0.5 mg/mL.

8. The liquid formulation according to claim 1, wherein the liquid formulation has a pH value of 6.0.

9. The liquid formulation according to claim 1, wherein the liquid formulation comprises no antioxidant; and/or, the liquid formulation comprises no viscosity reducer.

10. The liquid formulation according to claim 1, wherein the liquid formulation comprises:
    the anti-IL-17 antibody at a concentration of 100 mg/mL;
    the citrate buffer at a concentration of 20 mM;
    sucrose at a concentration of 80 mg/ml or arginine at a concentration of 150 mM; and
    polysorbate 80 at a concentration of 0.5 mg/mL, and
    wherein the liquid formulation has a pH value of 6.0.

11. The liquid formulation according to claim 10, wherein the citrate buffer is citric acid-sodium citrate buffer.

12. The liquid formulation according to claim 10, wherein the citrate buffer consists of 0.66 mg/mL citric acid and 4.95 mg/mL sodium citrate dihydrate.

13. The liquid formulation according to claim 10, wherein the liquid formulation is in the form of a solution, an emulsion, or a suspension.

14. The liquid formulation according to claim 1, wherein the liquid formulation is a pharmaceutical formulation of the anti-IL-17 antibody.

15. The liquid formulation according to claim 14, wherein the liquid formulation is in the form of a solution, an emulsion, or a suspension.

16. A kit comprising the liquid formulation according to claim 1 in a container.

* * * * *